United States Patent [19]

Davis

[11] 4,140,643
[45] Feb. 20, 1979

[54] NITROGEN- AND SULFUR-CONTAINING LUBRICANT ADDITIVE COMPOSITIONS OF IMPROVED COMPATIBILITY

[75] Inventor: Kirk E. Davis, Euclid, Ohio

[73] Assignee: The Lubrizol Corporation, Wickliffe, Ohio

[21] Appl. No.: 803,179

[22] Filed: Jun. 3, 1977

Related U.S. Application Data

[63] Continuation-in-part of Ser. No. 470,483, May 16, 1974, which is a continuation-in-part of Ser. No. 459,428, Apr. 9, 1974, abandoned, which is a continuation-in-part of Ser. No. 380,914, Jul. 19, 1973, abandoned.

[51] Int. Cl.$^2$ .............................................. C10M 1/38
[52] U.S. Cl. ............................... 252/47.5; 260/302 D; 260/302 SD
[58] Field of Search ................ 252/47.5; 260/302 SD, 260/302 D

[56] References Cited

U.S. PATENT DOCUMENTS

| | | | |
|---|---|---|---|
| 2,355,995 | 8/1944 | Morgan et al. | 252/56 R |
| 2,764,547 | 9/1956 | Fields | 252/32.7 |
| 2,910,439 | 10/1959 | Fields | 252/46.7 |
| 3,050,466 | 8/1962 | Heisig et al. | 252/56 R |
| 3,208,945 | 9/1965 | Stuart et al. | 252/56 D |
| 3,519,564 | 7/1970 | Vogel | 252/47.5 |
| 3,533,943 | 10/1970 | Papay | 252/32.7 |
| 3,630,902 | 12/1971 | Coupland et al. | 252/51.5 R |
| 3,630,903 | 12/1971 | Hellmuth | 252/51.5 R |
| 3,630,904 | 12/1971 | Musser et al. | 252/51.5 R |
| 3,775,321 | 11/1973 | Turnquest | 252/42.7 |
| 3,840,549 | 10/1974 | Blaha et al. | 260/302 SD |
| 3,977,986 | 8/1976 | Conte, Jr. | 252/47.5 |

FOREIGN PATENT DOCUMENTS

| | | | |
|---|---|---|---|
| 965403 | 4/1975 | Canada | 252/47.5 |
| 809001 | 2/1959 | United Kingdom | 252/47.5 |
| 1462287 | 1/1977 | United Kingdom | 252/47.5 |

*Primary Examiner*—Delbert E. Gantz
*Assistant Examiner*—Andrew Metz
*Attorney, Agent, or Firm*—James W. Adams, Jr.; William H. Pittman; S. I. Khayat

[57] ABSTRACT

Nitrogen- and sulfur-containing compositions are prepared by reacting an oil-soluble dispersant with a dimercaptothiadiazole such as 2,5-dimercapto-1,3,4-thiadiazole and subsequently reacting the intermediate thus formed with a carboxylic acid or anhydride containing up to about 10 carbon atoms and having at least one olefinic bond. The preferred carboxylic acid or anhydride is maleic anhydride. The compositions thus obtained are useful in lubricants as dispersants, extreme pressure agents, corrosion inhibitors and inhibitors of copper activity and "lead paint" deposition.

20 Claims, No Drawings

NITROGEN- AND SULFUR-CONTAINING LUBRICANT ADDITIVE COMPOSITIONS OF IMPROVED COMPATIBILITY

CROSS-REFERENCE TO RELATED APPLICATIONS

The present application is a continuation-in-part of my co-pending application Ser. No. 470,483 filed on May 16, 1974, which itself was a continuation-in-part of then co-pending application Ser. No. 459,428 filed Apr. 9, 1974 which in turn was a continuation-in-part of then co-pending application Ser. No. 380,914 filed July 19, 1973. The last two applications are now abandoned.

This invention relates to new compositions of matter useful as multi-purpose additives in lubricants, and to lubricants containing said compositions. Briefly described, the invention comprises compositions prepared by:

(A) Preparing a mixture comprising at least one oil-soluble dispersant and at least one dimercaptothiadiazole and heating said mixture at a temperature above about 100° C. to convert it into an intermediate capable of forming a homogeneous blend with an oleaginous liquid of lubricating viscosity; and (B) Reacting said intermediate, at a temperature within the range of about 50°–200° C., with at least one carboxylic acid or anhydride containing up to about 10 carbon atoms and having at least one olefinic bond.

The use of lubricant additives containing dimercaptothiadiazole groups, especially 2,5-dimercapto-1,3,4-thiadiazole, to suppress copper activity and "lead paint" deposition is known. Particular reference is made to my copending application Ser. No. 470,483, now British Pat. No. 1,462,287, which describes multi-purpose additives prepared by reacting the dimercaptothiadiazole with an oil-soluble dispersant. Such materials may also serve as extreme pressure agents and corrosion inhibitors for copper-lead bearings and have dispersant properties owing to the presence of dispersant moieties therein.

A problem sometimes encountered in additive-containing lubricants is that of compatibility between the various additives used. Occasionally it is found that the presence of a particular additive or combination of additives decreases somewhat the solubilities of other additives in the lubricant, resulting in the formation of haze or sediment during storage. Such haze or sediment formation is, of course, undesirable since the insoluble material may be deposited on engine parts or elsewhere in the machine being lubricated and the oil contains less additive than is proper.

A principal object of the present invention, therefore, is to provide improved multi-purpose additives for lubricants.

A further object is to provide additives which are compatible with a wide variety of other additives.

Still another object is to provide nitrogen- and sulfur-containing lubricant additives which suppress copper activity and "lead paint" formation and also have dispersant properties and other beneficial properties.

Other objects will in part be obvious and will in part appear hereinafter.

As previously noted, the compositions of this invention are prepared by a two-step method in which the first step (step A) is the preparation of a dispersant-dimercaptothiadiazole intermediate. The method for the preparation of this intermediate is described in detail in the above-mentioned British Pat. No. 1,462,287, which is incorporated by reference herein for its description thereof.

The dimercaptothiadiazole used in step A is preferably 2,5-dimercapto-1,3,4-thiadiazole, referred to sometimes hereinafter as DMTD. The oil-soluble dispersant is usually one of the materials known in the art as "ashless dispersants", although, depending on its constitution, the dispersant may upon combustion yield a non-volatile material such as boric oxide or phosphorus pentoxide; however, it does not ordinarily contain metal and therefore does not yield a metal-containing ash on combustion.

Oil-soluble dispersants of many types are known in the art and are described in various patents. Any of them are suitable for use in preparing the intermediate. The following are illustrative:

(1) Reaction products of carboxylic acids (or derivatives thereof) containing at least about 34 and preferably at least about 54 carbon atoms with nitrogen-containing compounds such as amines, organic hydroxy compounds such as phenols and alcohols, and/or basic inorganic materials. Examples of these products, referred to herein as "carboxylic dispersants", are described in British Pat. No. 1,306,529 and in many U.S. patents including the following:

| | | |
|---|---|---|
| 3,163,603 | 3,351,552 | 3,541,012 |
| 3,184,474 | 3,381,022 | 3,542,678 |
| 3,215,707 | 3,399,141 | 3,542,680 |
| 3,219,666 | 3,415,750 | 3,567,637 |
| 3,271,310 | 3,433,744 | 3,574,101 |
| 3,272,746 | 3,444,170 | 3,576,743 |
| 3,281,357 | 3,448,048 | 3,630,904 |
| 3,306,908 | 3,448,049 | 3,632,510 |
| 3,311,558 | 3,451,933 | 3,632,511 |
| 3,316,177 | 3,454,607 | 3,697,428 |
| 3,340,281 | 3,467,668 | 3,725,441 |
| 3,341,542 | 3,501,405 | Re 26,433 |
| 3,346,493 | 3,522,179 | |

(2) Reaction products of aliphatic or alicyclic halides containing at least about 30 carbon atoms with amines, preferably polyalkylene polyamines. These may be characterized as "amine dispersants" and examples thereof are described, for example, in the following U.S. patents:

| | |
|---|---|
| 3,275,554 | 3,454,555 |
| 3,438,757 | 3,565,804 |

(3) Reaction products of alkyl phenols in which the alkyl group contains at least about 30 carbon atoms with aldehydes (especially formaldehyde) and amines (especially polyalkylene polyamines), which may be characterized as "Mannich dispersants". The materials described in the following U.S. patents are illustrative:

| | |
|---|---|
| 3,413,347 | 3,725,480 |
| 3,697,574 | 3,726,882 |
| 3,725,277 | |

(4) Products obtained by post-treating the carboxylic, amine or Mannich dispersants with such reagents as sulfur, urea, thiourea, carbon disulfide, aldehydes, ketones, carboxylic acids, hydrocarbon-substituted succinic anhydrides, nitriles, epoxides, boron compounds, phosphorus compounds or the like. Exemplary materials of this kind are described in the following U.S. patents:

| | | | |
|---|---|---|---|
| 3,036,003 | 3,282,955 | 3,493,520 | 3,639,242 |
| 3,087,963 | 3,312,619 | 3,502,677 | 3,649,229 |
| 3,200,107 | 3,366,569 | 3,513,093 | 3,649,659 |
| 3,216,963 | 3,367,943 | 3,533,945 | 3,658,836 |
| 3,254,025 | 3,373,111 | 3,539,633 | 3,697,574 |
| 3,256,185 | 3,403,102 | 3,573,010 | 3,702,757 |
| 3,278,550 | 3,442,808 | 3,579,450 | 3,703,536 |
| 3,280,234 | 3,455,831 | 3,591,598 | 3,704,308 |
| 3,281,428 | 3,455,832 | 3,600,372 | 3,708,522 |

(5) Interpolymers of oil-solubilizing monomers containing a pendant alkyl group having at least about 8 carbon atoms, such as decyl methacrylate, vinyl decyl ether or a relatively high molecular weight olefin, with monomers containing polar substituents, e.g., aminoalkyl acrylates, aminoalkyl acrylamides or poly-(oxyalkylene)-substituted alkyl acrylates. These may be characterized as "polymeric dispersants" and examples thereof are disclosed in the following U.S. patents:

| | |
|---|---|
| 3,329,658 | 3,666,730 |
| 3,449,250 | 3,687,849 |
| 3,519,565 | 3,702,300 |

The pertinent disclosures of all of the above-noted patents are incorporated by reference herein.

The carboxylic dispersants are the preferred ones for use in the preparation of the compositions of this invention. They may be most conveniently and accurately described in terms of radicals 1 and 2 present therein. Radical 1 is at least one acyl, acyloxy or acylimidoyl radical containing at least about 34 carbon atoms. The structures of these radicals, as defined by the International Union of Pure and Applied Chemistry, are as follows (R representing a hydrocarbon or similar group):

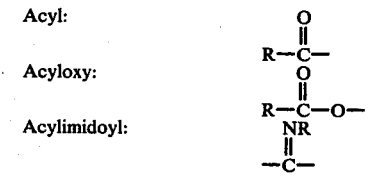

Radical 2 is preferably at least one radical in which a nitrogen or oxygen atom is attached directly to said radical 1, said nitrogen or oxygen atom also being attached to a hydrocarbon radical or substituted hydrocarbon radical, especially an amino, alkylamino-, polyalkyleneamino-, hydroxy- or alkyleneoxy-substituted hydrocarbon radical. With respect to radical 2, the dispersants are conveniently classified as "nitrogen-bridged dispersants" and "oxygen-bridged dispersants" wherein the atom attached directly to radical 1 is nitrogen or oxygen, respectively.

The nitrogen-bridged dispersants, which will be described first, are those disclosed (for example) in the above-mentioned U.S. Pat. Nos. 3,219,666 and 3,272,746 which also describe a large number of methods for their preparation. The nitrogen-containing group therein is derived from compounds characterized by a radical of the structure > NH wherein the two remaining valences of nitrogen are satisfied by hydrogen, amino or organic radicals bonded to said nitrogen atom through direct carbon-to-nitrogen linkages. These compounds include aliphatic, aromatic, heterocyclic and carbocyclic amines as well as substituted ureas, thioureas, hydrazines, guanidines, amidines, amides, thioamides, cyanamides and the like.

Especially preferred as nitrogen-containing compounds used in the preparation of the nitrogen-bridged dispersants are alkylene polyamines and hydroxyalkyl-substituted alkylene polyamines. The alkylene polyamines comprise, in general, alkylene amines containing about 10 or less alkylene groups joined through nitrogen atoms. They include principally the ethylene amines, propylene amines, butylene amines and homologs thereof, and also piperazines and aminoalkyl-substituted piperazines. Hydroxyalkyl-substituted derivatives of these alkylene polyamines are also contemplated for use in preparing the nitrogen-bridged dispersant. Typical examples of suitable amines are ethylene diamine, triethylene tetramine, pentaethylene hexamine, propylene diamine, tripropylene tetramine, di-(trimethylene)triamine, 1,4-bis-(2-aminoethyl)piperazine, 1-(2-aminopropyl)piperazine, N-(2-hydroxyethyl)ethylene diamine, 1-(2-hydroxyethyl)piperazine, and 2-heptadecyl-1-(2-hydroxyethyl)-imidazoline. Mixtures of these amines may also be used.

The preferred amines are the polyethylene polyamines containing from two to about eight amino groups per molecule. A commercially available mixture of polyethylene polyamines containing an average of about 3-7 amino groups per molecule is particularly suitable.

The acylating agent used for preparing the nitrogen-bridged dispersant is a carboxylic acid-producing compound containing at least about 34 and preferably at least about 54 carbon atoms. By "carboxylic acid-producing compound" is meant an acid, anhydride, acid halide, ester, amide, imide, amidine or the like; the acids and anhydrides are preferred.

The acylating agent is usually prepared by the reaction (more fully described hereinafter) of a relatively low molecular weight carboxylic acid-producing compound with a hydrocarbon-based source containing at least about 30 and preferably at least about 50 carbon atoms. The hydrocarbon-based source should be substantially saturated, i.e., at least about 95% of the total number of carbon-to-carbon covalent linkages should be saturated. It should also be substantially free from pendant groups containing more than about six aliphatic carbon atoms.

As used herein, the term "hydrocarbon-based" denotes a radical which, upon reaction as described hereinafter, will have a carbon atom directly attached to the remainder of the molecule and which has predominantly hydrocarbon character within the context of this invention. Such radicals include the following:

(1) Hydrocarbon radicals; that is, aliphatic, (e.g., alkyl or alkenyl), alicyclic (e.g., cycloalkyl or cycloalkenyl), aromatic, aliphatic- and alicyclic-substituted aromatic, aromatic-substituted aliphatic and alicyclic radicals, and the like, as well as cyclic radicals wherein the ring is completed through another portion of the molecule (that is, any two indicated substituents may together form an alicyclic radical).

(2) Substituted hydrocarbon radicals; that is, radicals containing non-hydrocarbon substituents which, in the context of this invention, do not alter the predominantly hydrocarbon character of the radical but which frequently act as activating radicals for the reaction with the low molecular weight acid-producing compound as described hereinafter. Those skilled in the art will be aware of suitable substituents; examples are halo, hydroxy, ether, aldehydo, keto, carboxy, ester (especially lower carbalkoxy), amide, nitro, cyano, mercaptan, sulfide, disulfide, sulfoxy and sulfone. Halo and especially chloro substituents are preferred.

(3) Hetero radicals; that is, radicals which, while predominantly hydrocarbon in character within the context of this invention, contain atoms other than carbon present in a chain or ring otherwise composed of carbon atoms. Suitable hetero atoms will be apparent to those skilled in the art and include, for example, nitrogen, oxygen and sulfur.

In general, no more than about three substituents or hetero atoms, and preferably no more than one, will be present for each 10 carbon atoms in the hydrocarbon-based radical.

The preferred hydrocarbon sources are those derived from substantially saturated petroleum fractions and olefin polymers, particularly polymers of monoolefins having from 2 to about 30 carbon atoms. Thus, the hydrocarbon source may be derived from a polymer of ethylene, propene, 1-butene, isobutene, 1-octene, 3-cyclohexyl-1-butene, 2-butene, 3-pentene or the like. Also useful are interpolymers of olefins such as those illustrated above with other polymerizable olefinic substances such as styrene, chloroprene, isoprene, p-methylstyrene, piperylene and the like. In general, these interpolymers should contain at least about 80%, preferably at least about 95%, on a weight basis of units derived from the aliphatic monoolefins.

Another suitable hydrocarbon source comprises saturated aliphatic hydrocarbons such as highly refined high molecular weight white oils or synthetic alkanes.

As already pointed out, the hydrocarbon-based source generally contains at least about 30 and preferably at least about 50 carbon atoms. Among the olefin polymers those having a molecular weight of about 700–5000 are preferred, although higher polymers having molecular weights from about 10,000 to about 100,000 or higher may sometimes be used. Especially suitable as hydrocarbon-based sources are butene polymers within the prescribed molecular weight range containing predominantly isobutene units, and chlorinated derivatives thereof.

Any one of a number of known reactions may be employed for the incorporation of the hydrocarbon-based source into the acid-producing compound to provide the required acylating agent. Thus, an alcohol of the desired molecular weight may be oxidized with potassium permanganate, nitric acid or a similar oxidizing agent; a halogenated olefin polymer may be reacted with a ketene; an ester of an active hydrogen-containing acid, such as acetoacetic acid, may be converted to its sodium derivative and the sodium derivative reacted with a halogenated high molecular weight hydrocarbon such as brominated wax or brominated polybutene; a high molecular weight olefin may be ozonized; a methyl ketone of the desired molecular weight may be oxidized by means of the haloform reaction; an organo-metallic derivative of a halogenated hydrocarbon may be reacted with carbon dioxide; a halogenated hydrocarbon or olefin polymer may be converted to a nitrile, which is subsequently hydrolyzed; or an olefin polymer or its halogenated derivative may undergo an addition reaction with an unsaturated acid or derivative thereof. This latter reaction is preferred, especially where the acid-producing compound is maleic acid or anhydride. The resulting product is then a hydrocarbon-substituted succinic acid or derivative thereof. The reaction leading to its formation involves merely heating the two reactants at about 100°–200° C. The substituted succinic acid or anhydride thus obtained, may, if desired, be converted to the corresponding acid halide by reaction with known halogenating agents such as phosphorus trichloride, phosphorus pentachloride or thionyl chloride.

For the formation of the nitrogen-bridged dispersant, the hydrocarbon-substituted succinic anhydride or acid, or other acylating agent, and the alkylene polyamine or other nitrogen-containing reagent are heated to a temperature above about 80° C., preferably about 100°–250° C. The product thus obtained has predominantly amide, imide and/or amidine linkages (containing acyl or acylimidoyl groups). The process may in some instances be carried out at a temperature below 80° C. to produce a product having predominantly salt linkages (containing acyloxy groups). The use of a diluent such as mineral oil, benzene, toluene, naphtha or the like is often desirable to facilitate control of the reaction temperature.

The relative proportions of the acylating agent and the alkylene polyamine or the like are such that at least about one-half the stoichiometrically equivalent amount of polyamine is used for each equivalent of acylating agent. In this regard, it will be noted that the equivalent weight of the alkylene polyamine is based upon the number of amine radicals therein, and the equivalent weight of the acylating agent is based on the number of acidic or potentially acidic radicals. (Thus, the equivalent weight of a hydrocarbon-substituted succinic acid or anhydride is one-half its molecular weight.) Although a minimum of one-half equivalent of polyamine per equivalent of acylating agent should be used, there does not appear to be an upper limit for the amount of polyamine. If an excess is used, it merely remains in the product unreacted without any apparent adverse effects. Ordinarily, no more than about 2 equivalents of polyamine are used per equivalent of acylating agent.

Especially preferred for the purposes of this invention are substantially neutral or acidic dispersants; that is, dispersants having a base number less than 7 or an acid number when titrated to a bromphenol blue end point. ("Acid number" is the number of milligrams of potassium hydroxide required for titration of a 1-gram sample, and "base number" is the number of milligrams of potassium hydroxide equivalent to the amount of acid required for titration of a 1-gram sample.) Nitrogen-bridged dispersants of this type may often be prepared by using one equivalent or less of polyamine per equivalent of acylating agent.

In an alternative method for producing the nitrogen-bridged dispersant, the alkylene polyamine is first reacted with a low molecular weight, unsaturated carboxylic acid-producing compound such as maleic anhydride and the resulting intermediate is subsequently reacted with the hydrocarbon source as previously described.

Oxygen-bridged dispersants comprise the esters of the above-described carboxylic acids, as described (for example) in the aforementioned U.S. Pat. Nos. 3,381,022 and 3,542,678. As such, they contain acyl or, occasionally, acylimidoyl radicals as radical 1. (An oxygen-bridged dispersant containing an acyloxy radical as radical 1 would be a peroxide, which is unlikely to be stable under all conditions of use of the compositions of this invention.) These esters are preferably prepared by conventional methods, usually the reaction (frequently in the presence of an acidic catalyst) of the carboxylic acid-producing compound with an aliphatic compound such as a monohydric or polyhydric alcohol or with an aromatic compound such as a phenol or naphthol. The preferred hydroxy compounds are alcohols containing up to about 40 aliphatic carbon atoms. These may be monohydric alcohols such as methanol, ethanol, isooctanol, dodecanol, cyclohexanol, neopentyl alcohol, monomethyl ether of ethylene glycol and the like, or polyhydric alcohols including ethylene glycol, diethylene glycol, dipropylene glycol, tetramethylene glycol, pentaerythritol, glycerol and the like. Carbohydrates (e.g., sugars, starches, cellulose) and also suitable as are partially esterified derivatives of polyhydric alcohols having at least three hydroxy radicals.

The reaction is usually effected at a temperature above about 100° C. and typically at 150°–300° C. The esters may be neutral or acidic, or may contain unesterified hydroxy groups, according as the ratio of equivalents of acid-producing compound to hydroxy compound is equal to, greater than or less than 1:1.

As will be apparent, the oxygen-bridged dispersants are normally substantially neutral or acidic. They are among the preferred dispersants for the purposes of this invention.

It is possible to prepare mixed oxygen- and nitrogen-bridged dispersants by reacting the acylating agent simultaneously or, preferably, sequentially with nitrogen-containing and hydroxy reagents such as those previously described. The relative amounts of the nitrogen-containing and hydroxy reagents may be between about 10:1 and 1:10, on an equivalent weight basis. The methods of preparation of the mixed oxygen- and nitrogen-bridged dispersants are generally the same as for the individual dispersants described, except that two sources of radical 2 are used. As previously noted, substantially neutral or acidic dispersants are preferred, and a typical method of producing mixed oxygen- and nitrogen-bridged dispersants of this type (which are especially preferred) is to react the acylating agent with the hydroxy reagent first and subsequently react the intermediate thus obtained with a suitable nitrogen-containing reagent in an amount to afford a substantially neutral or acidic product.

Typical carboxylic dispersants suitable for use in preparing the intermediate are listed in Table I. "Reagent 1" and "Reagent 2" are, respectively, the sources of radicals 1 and 2 as previously defined. The dispersants of Examples 1–6, 8, 9, 12 and 14–17 are basic; those of the other examples are substantially neutral or acidic.

TABLE I

| Example | Reagent 1 | Reagent 2 | Ratio of equivalents, 1:2 | Reaction temperature, °C. | Diluent | Acid or base no. |
|---|---|---|---|---|---|---|
| 1 | Polyisobutenyl (mol. wt.) about 900) succinic anhydride prepared from chlorinated polyisobutene | Polyethylene amine mixture containing about 3–7 amino groups per molecule | 0.48 | 150 | Mineral oil | 50B |
| 2 | Same as Example 1 | Pentaethylene hexamine | 0.41 | 150 | Mineral oil | 82B |
| 3 | Like Example 1 except polyisobutene mol. wt. is about 1050 | Pentaethylene hexamine | 0.61 | 150 | Mineral oil | 130B |
| 4 | Like Example 1, except polyisobutene mol. wt. is about 850 | Diethylene triamine | 1.0 | 150 | Mineral oil | 19B |
| 5 | Same as Example 4 | Ethylene diamine | 1.0 | 150 | Mineral oil | 19B |
| 6 | Same as Example 4 | Di-(1,2-propylene) triamine | 1.0 | 180–190 | Mineral oil-toluene | — |
| 7 | Same as Example 4 | N-(2-hydroxyethyl)-trimethylene diamine | 1.06 | 150–155 | Mineral oil | 4A |
| 8 | Tetrapropenyl succinic anhydride | Triethylene tetramine | 1.0 | 155 | Toluene | 60B |
| 9 | Same as Example 1 | Same as Example 1 | 0.67 | 150 | Mineral oil | 35B |
| 10 | Same as Example 1 | Same as Example 1 | 1.33 | 150 | Mineral oil | 6B |
| 11 | Like Example 1, except polyisobutene mol. wt. is about 1100 | Pentaerythritol, followed by polyethylene amine of Example 1 (ratio of equivalents 7.7:1) | 0.44 | 150–210 | Mineral oil | 2B |
| 12 | Isostearic acid | Pentaethylene hexamine | 0.8 | 150 | Mineral oil | 8B |
| 13 | Acid produced by reaction of chlorinated (3.6% Cl) polyisobutene (mol. wt. 750) with KCN, followed by hydrolysis | Ethylene diamine | 2.0 | 150 | Xylene | — |
| 14 | Methyl ester produced by reaction of chlorinated (4.7% Cl) polyisobutene (mol. wt. 1000) with methyl methacrylate | Triethylene tetramine | 1.0 | 140–220 | — | — |
| 15 | Reaction product of sodiomalonic ester with $C_{75}$ brominated wax | Same as Example 1 | 0.4 | 150 | Xylene | — |
| 16 | Reaction product of chlorinated (4.5% Cl) polyisobutene (mol. wt. 850) with acrylic acid | Pentaethylene hexamine | 0.8 | 180–200 | — | — |
| 17 | Acid produced by haloform reaction with methyl heptacontanyl ketone | Same as Example 1 | 0.8 | 180–210 | — | — |
| 18 | Same as Example 11 | Pentaerythritol | 0.5 | 150–210 | Mineral oil | — |
| 19 | Like Example 1, except polyisobutene mol. wt. is about 1000 | Neopentyl glycol | 1.0 | 240–250 | — | — |
| 20 | Same as Example 19 | Methanol* | Excess methanol | 50–65 | Toluene | — |
| 21 | Same as Example 19 | Polyethylene glycol | 2.0 | 240–250 | — | — |

TABLE I-continued

| Example | Reagent 1 | Reagent 2 | Ratio of equivalents, 1:2 | Reaction temperature, °C. | Diluent | Acid or base no. |
|---|---|---|---|---|---|---|
| 22 | Same as Example 19 | (mol. wt. about 600) Oleyl alcohol** | 1.0 | 150–173 | Xylene | 0 |
| 23 | Like Example 16, except polyisobutene mol. wt. is about 982 | Sorbitol | 0.48 | 115–205 | Mineral oil | — |
| 24 | Same as Example 23 | Pentaerythritol | 1.0 | 180–205 | — | — |
| 25 | Reaction product of polyisobutene (mol. wt. 1500) with chloroacetyl chloride | Mannitol | 0.33 | 115–205 | Mineral oil | — |

*Hydrogen chloride catalyst
**p-Toluenesulfonic acid catalyst

The intermediate is formed by preparing a mixture of DMTD and the dispersant and heating said mixture at a temperature above about 100° C., usually about 100°–250° and especially about 120°–200°, for a period of time sufficient to provide a product which is capable of forming a homogeneous blend with an eleaginous liquid of lubricating viscosity, such as a lubricating oil or synthetic lubricant. The mixture will usually also contain an organic liquid diluent which may be either polar or non-polar.

The relative amounts of dispersant and DMTD in the intermediate may vary widely, as long as a homogeneous product is ultimately obtained. Thus, about 0.1–10 parts by weight of dispersant may be used per part of DMTD. Most often, about 5–10 parts of dispersant are used per part of DMTD. The product usually contains DMTD moieties in amounts substantially greater than the stoichiometric amount based on salt formation. If the dispersant is neutral or acidic there is, of course, no "stoichiometric amount" of DMTD and any amount thereof in the product is present in excess. If the dispersant is basic, the product usually contains at least about a five-fold excess and may contain a 500-fold or even greater excess of DMTD moieties, based on the stoichiometric amount.

The preparation of the intermediate is illustrated by the following examples. All parts and percentages are by weight. The weight ratios of dispersant to DMTD referred to are, in each instance, initial ratios. Equivalents of base in the dispersant are calculated from the base number.

EXAMPLE 26

Six thousand parts of the dispersant of Example 10 (0.64 equivalent of base) is heated to 100° C., and 484 parts of wet DMTD (420 parts on a dry basis, or 5.6 equivalents) is added over 15 minutes, with stirring. The mixture is heated at 110°–120° for 6 hours under nitrogen, during which time hydrogen sulfide evolution is noted. Mineral oil, 1200 parts, is added and the mixture is filtered while hot. The filtrate is a 53% solution of the desired intermediate in oil and contains 1.68% nitrogen and 2.83% sulfur. The weight ratio of dispersant to DMTD is 8.6.

EXAMPLE 27

DMTD (5.6 equivalents) is prepared by adding 447 parts of carbon disulfide over 2¾ hours to a mixture of 140 parts of hydrazine hydrate, 224 parts of 50% aqueous sodium hydroxide and 1020 parts of mineral oil, with stirring under nitrogen at 25°–46° C., heating the resulting mixture at 96°–104° C. for about 3 hours, and then cooling to 78° C. and acidifying with 280 parts of 50% aqueous sulfuric acid. The resulting material is heated to 94° C., and 6000 parts of the dispersant of Example 10 (0.64 equivalent of base) is added over about ½ hour at 90°–94° C., under nitrogen. The mixture is heated gradually to 150° C., and maintained at that temperature for about 3 hours; it is then filtered while hot to yield a 50% solution in mineral oil of the desired intermediate. The solution contains 2.06% nitrogen and 3.26% sulfur, and the weight ratio of dispersant to DMTD therein is 8.6.

EXAMPLE 28

One thousand parts of the dispersant of Example 1 (0.89 equivalent of base) is heated to 95° C., under nitrogen, and 288 parts of wet DMTD (250 parts of a dry basis, or 3.33 equivalents) is added over about 20 minutes. The mixture is heated to 150° C., and held at that temperature for about 5 hours, and is then filtered while hot to yield the desired intermediate, a 59% solution in oil containing 4.61% nitrogen and 9.19% sulfur. The weight ratio of dispersant to DMTD is 2.4.

EXAMPLE 29

Following the procedure of Example 28, a product is prepared from 200 parts each of the dispersant of Example 1 (0.18 equivalent of base) and DMTD (2.67 equivalents), and 2000 parts of mineral oil is added. The intermediate (a 20% solution in oil) contains 1.12% nitrogen and 3.48% sulfur, and the weight ratio of dispersant to DMTD is 0.6.

EXAMPLE 30

Following the procedure of Example 28, an intermediate (50% solution in oil) is prepared from 7300 parts of the dispersant of Example 11 (0.26 equivalent of base), 588 parts of wet DMTD (510 parts on a dry basis, or 6.8 equivalents) and 1250 parts of mineral oil. It contains 1.72% nitrogen and 3.08% sulfur, and the weight ratio of dispersant to DMTD is 7.86.

EXAMPLE 31

Following the procedure of Example 28, an intermediate is prepared from 1000 parts of the dispersant of Example 11 (0.036 equivalent of base), 241 parts (3.21 equivalents) of DMTD and 310 parts of mineral oil. The product is a 50% solution in mineral oil and contains 2.74% nitrogen and 6.79% sulfur. The ratio of dispersant to DMTD is 2.62.

EXAMPLE 32

Following the procedure of Example 27, DMTD (8.16 equivalents) is prepared from 204 parts of hydrazine hydrate, 324 parts of 50% aqueous sodium hydroxide, 648 parts of carbon disulfide, 1200 parts of mineral oil and 408 parts of 50% aqueous sulfuric acid. It is then reacted with 600 parts of the dispersant of Example 11 (0.02 equivalent of base) in the presence of 600 parts of toluene, and the toluene and water are removed by azeotropic distillation to yield an intermediate (50% solution in mineral oil) containing 1.8% nitrogen and 5.1% sulfur, and having a 5.5:1 ratio of dispersant to DMTD.

EXAMPLE 33

Following the procedure of Example 27, DMTD (5.6 equivalents) is prepared from 140 parts of hydrazine hydrate, 447 parts of carbon disulfide, 224 parts of 50% aqueous sodium hydroxide, 280 parts of 50% aqueous sulfuric acid and 1020 parts of mineral oil. It is then reacted with 6000 parts of the dispersant of Example 11 (0.22 equivalent of base) to yield an intermediate (50% solution in oil) containing 1.35% nitrogen and 2.64% sulfur, and having a weight ratio of dispersant to DMTD of 7.86.

EXAMPLE 34

Hydrazine hydrate, 28 parts, is mixed with 45 parts of 50% aqueous sodium hydroxide and 206 parts of mineral oil, and 102 parts of carbon disulfide is added over 2 hours. An exothermic reaction takes place which causes the temperature to rise to 38° C. The mixture is heated to 109° C., and maintained at that temperature for 1 hour, during which time hydrogen sulfide evolution is noted. It is then cooled to 88° C., and 88 parts of 33% aqueous sulfuric acid is added over ½ hour. The temperature rises to 90° C. during this addition.

The resulting slurry (1.12 equivalents of DMTD) is added to 1209 parts (0.043 equivalent of base) of the dispersant of Example 11. Volatile materials are removed by vacuum stripping at 150° C., and the remaining mixture is heated for 3 hours at that temperature. The residue is filtered while hot and the filtrate is the desired intermediate (51% solution in oil) containing 1.43% nitrogen and 2.90% sulfur, and having a weight ratio if dispersant to DMTD of 7.86.

EXAMPLE 35

A mixture of 1000 parts of the dispersant of Example 11 (0.036 equivalent of base) and 170 parts of mineral oil is heated to 70° C., and a solution of 70 parts (0.93 equivalent) of DMTD in 865 parts of isopropyl alcohol is added over about ½ hour, with stirring. Heating at 70° C. is continued as the isopropyl alcohol is stripped under vacuum, yielding a homogeneous mixture. This mixture is gradually heated to 155° C.; during the heating, a solid precipitates and a sample thereof is removed and analyzed. Elemental analysis indicates that it is an oligomer of DMTD, principally a dimer.

As heating continues above 140° C., the solid is gradually solubilized to yield a homogeneous material again. This material is the desired intermediate (50% solution in oil) having a dispersant to DMTD ratio of 7.86:1.

In step B of the method for preparing the compositions of this invention, the intermediate whose preparation is described hereinabove is reacted with at least one carboxylic acid or anhydride containing up to about 10 (preferably about 4–8) carbon atoms and having at least one (and usually only one) olefinic bond. The carboxylic acid is usually an aliphatic carboxylic acid, most often one in which the aliphatic group is an aliphatic hydrocarbon radical. The olefinic bond is usually in a conjugated position with respect to the carboxylic acid group. Illustrative of suitable carboxylic acids are acrylic acid, methacrylic acid, 2-butenoic acid, 3-butenoic acid, maleic acid, itaconic acid and citraconic acid. The anhydrides of these acids are also useful and are frequently preferred. Especially preferred are the polycarboxylic acids and anhydrides, with maleic anhydride being particularly desirable because of its availability and suitability for the purposes of this invention.

The amount of carboxylic acid or anhydride used in step B is generally about 0.1–2.0 equivalents, and preferably about 0.2–1.0 equivalents, per equivalent of thiadiazole moieties in the intermediate. For this purpose, equivalents of acid or anhydride are based on the number of carboxylate groups per molecule. One equivalent of an intermediate containing DMTD moieties is an amount thereof which contains 150 parts by weight of such moieties (the molecular weight of DMTD being 150).

The temperature at which step B is effected is about 50°–200° C., and most often about 100°–150° C. The reaction is conducted within this temperature range for a period of time sufficient to complete the reaction.

Step B is usually conveniently carried out by merely blending the two reagents and heating for a suitable time, without any other materials being present apart from diluent accompanying the intermediate. The reaction may, however, be effected in the presence of other substantially inert, normally liquid organic diluents such as xylene, ethers or ether alcohols boiling within or above the temperature range required for the reaction, or the like. The composition of this invention is then obtained as a solution in the diluent or diluents used, from which solid foreign matter may be removed by conventional means such as filtration or centrifugation.

The molecular structures of the compositions of this invention are not known with certainty. It is believed that reaction takes place between free mercapto groups on the DMTD moiety and both the acidic and olefinic functions of the acid or anhydride. However, in view of the fact that the reaction as to either of these functional centers may not be complete, the composition formed may be a mixture of chemical species and its nature is therefore most accurately characterized in terms of the process for its preparation.

The preparation of the compositions of this invention is illustrated by the following examples. All parts are by weight.

EXAMPLE 36

A mixture of 710 parts (0.53 equivalent) of the intermediate of Example 34 and 3.14 parts of maleic anhydride is heated to 120° C. under nitrogen, with stirring, for about 1¾ hours. An additional 3.14 parts of maleic anhydride is added and heating is continued for an additional 5 hours, after which a final 1.57 parts of maleic anhydride (total 0.16 equivalent) is added and the mixture is heated for another 4½ hours. Volatile materials are stripped under vacuum at 126°–130° C., and the residual liquid is filtered to yield the desired product as an approximately 50% solution in oil.

EXAMPLE 37

A mixture of 447 parts (0.34 equivalent) of the intermediate of Example 34 and 10 parts (0.2 equivalent) of maleic anhydride is heated within the rage of 90°–150° C. for about 2 hours and is then vacuum stripped. The residual liquid is filtered to yield the desired product as a 51% solution in mineral oil.

EXAMPLE 38

Following the procedure of Example 37, a product is obtained by the reaction of 2000 parts (1.5 equivalents) of the intermediate of Example 34 and 10.5 parts (0.214 equivalent) of maleic anhydride.

EXAMPLE 39

An intermediate is prepared by the method of Example 34 except that the filtration step is omitted. To 8713 parts (6.56 equivalents) of this intermediate is added 93 parts (1.5 equivalents) of maleic anhydride and the mixture is heated at 145°–152° C. for 1 hour. It is then filtered to yield the desired product.

EXAMPLE 40

Following the procedure of Example 37, a product is made by reacting 0.34 equivalent of the intermediate of Example 26 with 0.2 equivalent of citraconic anhydride. A similar product is obtained.

EXAMPLE 41

Following the procedure of Example 37, 0.34 equivalent of the intermediate of Example 28 is reacted with 0.1 equivalent of acrylic acid. A similar product is obtained.

As previously indicated, the compositions of this invention are useful as additives for lubricants, in which they function primarily as copper activity and "lead paint" suppressants, dispersants, extreme pressure agents and corrosion inhibitors. They can be employed in a variety of lubricants based on diverse oils of lubricating viscosity, including natural and synthetic lubricating oils and mixtures thereof. These lubricants include crankcase lubricating oils for spark-ignited and compression-ignited internal combustion engines, including automobile and truck engines, two-cycle engines, aviation piston engines, marine and railroad diesel engines, and the like. They can also be used in gas engines, stationary power engines and turbines and the like. Automatic transmission fluids, transaxle lubricants, gear lubricants, metal-working lubricants, hydraulic fluids and other lubricating oil and grease compositions can also benefit from the incorporation therein of the compositions of the present invention.

Natural oils include animal oils and vegetable oils (e.g., castor oil, lard oil) as well as liquid petroleum oils and solvent-treated or acid-treated mineral lubricating oils of the paraffinic, naphthenic or mixed paraffinic-naphthenic types. Oils of lubricating viscosity derived from coal or shale are also useful base oils. synthetic lubricating oils include hydrocarbon oils and halosubstituted hydrocarbon oils such as polymerized and interpolymerized olefins [e.g., polybutylenes, polypropylenes, propylene-isobutylene copolymers, chlorinated polybutylenes, poly(1-hexenes), poly(1-octenes), poly(1-decenes), etc. and mixtures thereof]; alkylbenzenes (e.g., dodecylbenzenes, tetradecylbenzenes, dinonylbenzenes, di-(2-ethylhexyl)-benzenes, etc.); polyphenyls (e.g., biphenyls, terphenyls, alkylated polyphenyls, etc.), alkylated diphenyl ethers and alkylated diphenyl sulfides and the derivatives, analogs and homologs thereof and the like.

Alkylene oxide polymers and interpolymers and derivatives thereof where the terminal hydroxyl groups have been modified by esterification, etherification, etc. constitute another class of known synthetic lubricating oils. These are exemplified by the oils prepared through polymerization of ethylene oxide or propylene oxide, the alkyl and aryl ethers of these polyoxyalkylene polymers (e.g., methyl-polyisopropylene glycol ether having an average molecular weight of 1000, diphenyl ether of polyethylene glycol having a molecular weight of 500–1000, diethyl ether of polypropylene glycol having a molecular weight of 1000–1500, etc.) or mono- and polycarboxylic esters thereof, for example, the acetic acid esters, mixed $C_3$-$C_8$ fatty acid esters, or the $C_{13}$ Oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkyl malonic acids, alkenyl malonic acids, etc.) with a variety of alcohols (e.g., butyl alcohol, hexyl alcohol, dodecyl alcohol, 2-ethylhexyl alcohol, ethylene glycol, diethylene glycol monoether, propylene glycol, etc.). Specific examples of these esters include dibutyl adipate, di(2-ethylhexyl) sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, the complex ester formed by reacting one mole of sebacic acid with two moles of tetraethylene glycol and two moles of 2-ethylhexanoic acid, and the like.

Esters useful as synthetic oils also include those made from $C_5$ to $C_{12}$ monocarboxylic acids and polyols and polyol ethers such as neopentyl glycol, trimethylolpropane, pentaerythritol, dipentaerythritol, tripentaerythritol, etc.

Silicon-based oils such as the polyalkyl-, polyaryl-, polyalkoxy-, or polyaryloxy-siloxane oils and silicate oils comprise another useful class of synthetic lubricants (e.g., tetraethyl silicate, tetraisopropyl silicate, tetra(2-ethylhexyl) silicate, tetra-(4-methyl-2-ethylhexyl) silicate, tetra-(p-tert-butylphenyl) silicate, hexa-(4-methyl-2-pentoxy)-disiloxane, poly(methyl)siloxanes, poly(methylphenyl)siloxanes, etc.). Other synthetic lubricating oils include liquid esters of phosphorus-containing acids (e.g., tricresyl phosphate, trioctyl phosphate, diethyl ester of decylphosphonic acid, etc.), polymeric tetrahydrofurans and the like.

Unrefined, refined and rerefined oils (and mixtures of each with each other) of the type disclosed hereinabove can be used in the lubricant compositions of the present invention. Unrefined oils are those obtained directly from a natural or synthetic source without further purification treatment. For example, a shale oil obtained directly from retorting operations, a petroleum oil obtained directly from distillation or ester oil obtained directly from an esterification process and used without further treatment would be an unrefined oil. Refined oils are similar to the unrefined oils except they have been further treated in one or more purification steps to improve one or more properties. Many such purification techniques are known to those of skill in the art such as solvent extraction, acid or base extraction, filtration, percolation, etc. Rerefined oils are obtained by processes similar to those used to obtain refined oils applied to refined oils which have been already used in service. Such rerefined oils are also known as reclaimed or reprocessed oils and often are additionally processed by techniques directed to removal of spent additives and oil breakdown products.

Generally, the lubricants of the present invention contain an amount of the composition of this invention sufficient to provide it with the desired properties as described hereinabove. Normally this amount will be about 0.01–20.0%, preferably about 0.1–10.0%, of the total weight of the lubricant.

The invention also contemplates the use of other additives in combination with the compositions of this invention. Such additives include, for example, auxiliary detergents and dispersants of the ash-producing or ashless type, oxidation-inhibiting agents, auxiliary corrosion-inhibiting agents, pour point depressing agents, auxiliary extreme pressure agents, color stabilizers and anti-foam agents.

The ash-producing detergents are exemplified by oil-soluble neutral and basic salts of alkali or alkaline earth metals with sulfonic acids, carboxylic acids, or organic phosphorus acids characterized by at least one direct carbon-to-phosphorus linkage such as those prepared by the treatment of an olefin polymer (e.g., polyisobutene having a molecular weight of 1000) with a phosphorizing agent such as phosphorus trichloride, phosphorus heptasulfide, phosphorus pentasulfide, phosphorus trichloride and sulfur, white phosphorus and a sulfur halide, or phosphorothioic chloride. The most commonly used salts of such acids are those of sodium, potassium, lithium, calcium, magnesium, strontium and barium.

The term "basic salt" is used to designate metal salts wherein the metal is present in stoichiometrically larger amounts than the organic acid radical. The commonly employed methods for preparing the basic salts involve heating a mineral oil solution of an acid with a stoichiometric excess of a metal neutralizing agent such as the metal oxide, hydroxide, carbonate, bicarbonate, or sulfide at a temperature above 50° C., and filtering the resulting mass. The use of a "promoter" in the neutralization step to aid the incorporation of a large excess of metal likewise is known. Examples of compounds useful as the promoter include phenolic substances such as phenol, naphthol, alkylphenol, thiophenol, sulfurized alkylphenol, and condensation products of formaldehyde with a phenolic substance; alcohols such as methanol, 2-propanol, octyl alcohol, cellosolve, carbitol, ethylene glycol, stearly alcohol, and cyclohexyl alcohol; and amines such as aniline, phenylenediamine, phenothiazine, phenyl-β-naphthylamine, and dodecylamine. A particularly effective method for preparing the basic salts comprises mixing an acid with an excess of a basic alkaline earth metal neutralizing agent and at least one alcohol promoter, and carbonating the mixture at an elevated temperature such as 60°–200° C.

Auxiliary ashless detergents and dispersants are so called despite the fact that, depending on its constitution, the dispersant may upon combustion yield a non-volatile material such as boric oxide or phosphorus pentoxide; however, it does not ordinarily contain metal and therefore does not yield a metal-containing ash on combustion. Many types are known in the art and described hereinabove, and any of them are suitable for use in the lubricants of this invention.

Auxiliary extreme pressure and corrosion-inhibiting agents and oxidation-inhibiting agents are exemplified by chlorinated aliphatic hydrocarbons such as chlorinated wax; organic sulfides and polysulfides such as benzyl disulfide, bis(chlorobenzyl)disulfide, dibutyl tetrasulfide, sulfurized methyl ester of oleic acid, sulfurized alkylphenol, sulfurized dipentene, and sulfurized terpene; phosphosulfurized hydrocarbons such as the reaction product of a phosphorus sulfide with turpentine or methyl oleate; phosphorus esters including principally dihydrocarbon and trihydrocarbon phosphites such as dibutyl phosphite, diheptyl phosphite, dicyclohexyl phosphite, pentyl phenyl phosphite, dipentyl phenyl phosphite, tridecyl phosphite, distearyl phosphite, dimethyl naphthyl phosphite, oleyl 4-pentylphenyl phosphite, polypropylene (molecular weight 500)-substituted phenyl phosphite, diisobutyl-substituted phenyl phosphite; metal thiocarbamates, such as zinc dioctyldithiocarbamate, and barium heptylphenyl dithiocarbamate; Group II metal phosphorodithioates such as zinc dicyclohexylphosphorodithioate, zinc dioctylphosphorodithioate, barium di(heptylphenyl)-phosphorodithioate, cadmium dinonylphosphorodithioate, and the zinc salt of a phosphorodithioic acid produced by the reaction of phosphorus pentasulfide with an equimolar mixture of isopropyl alcohol and n-hexyl alcohol.

The compositions of this invention can be added directly to the lubricant. Preferably, however, they are diluted with a substantially inert, normally liquid organic diluent such as mineral oil, naphtha, benzene, toluene or xylene, to form an additive concentrate. These concentrates usually contain about 20–90% by weight of the composition of this invention and may contain, in addition, one or more other additives known in the art or described hereinabove.

Illustrative lubricants containing the compositions of this invention are listed in Table II. All parts are by weight. Except for the mineral oil base and the products of Examples 11 and 36–39, all amounts are exclusive of mineral oil used as diluent.

TABLE II

| Lubricant | Parts by weight | | | |
|---|---|---|---|---|
| | A | B | C | D |
| Mineral oil (10W-50 base) | 88.88 | 89.39 | 88.88 | 90.23 |
| Product of Example 36 | 1.00 | — | — | — |
| Product of Example 37 | — | 1.50 | — | — |
| Product of Example 38 | — | — | 1.00 | — |
| Product of Example 39 | — | — | — | 1.30 |
| Dispersant of Example 11 | 2.00 | — | 2.00 | — |
| Reaction product of polybutenyl (mol. wt. about 1000) succinic anhydride with polyhydric alcohol, polyalkylene glycol and ethylene polyamine | 1.98 | 2.81 | 1.98 | 2.92 |
| Basic calcium petroleum sulfonate | 0.94 | 0.94 | 0.94 | 0.94 |
| Zinc dialkylphosphorodithioate | 1.50 | 0.60 | 1.50 | 1.79 |
| Zinc di(alkylphenyl) phosphorodithioate | — | 1.06 | — | — |
| Polymeric viscosity index improver | 3.40 | 3.40 | 3.40 | 2.50 |
| Polymeric pour unit depressant | 0.30 | 0.30 | 0.30 | 0.30 |
| Polyalkylene glycol surfactant | — | — | — | 0.02 |
| Silicone anti-foam agent | 0.05 | — | 0.05 | 0.004 |

What is claimed is:
1. A composition prepared by:
(A) heating a mixture comprising at least one oil-soluble dispersant and at least one dimercaptothiadiazole at a temperature of above about 100° to about 250° C. to yield an intermediate capable of forming a homogeneous blend with an oleaginous liquid of lubricating viscosity, about 0.1–10 parts by weight of said dispersant being present per part of dimercaptothiadiazole; and
(B) reacting said intermediate, at a temperature within the range of about 50°–200° C., with at least one carboxylic acid or anhydride containing up to about 10 carbon atoms and having at least one olefinic bond.

2. A composition according to claim 1 wherein the dimercaptothiadiazole is 2,5-dimercapto-1,3,4-thiadiazole.

3. A composition according to claim 2 wherein the dispersant is selected from the group consisting of carboxylic dispersants, amine dispersants, Mannich dispersants, and polymeric dispersants.

4. A composition according to claim 3 wherein the dispersant is a carboxylic dispersant characterized by the presence within its molecular structure of (1) at least one acyl, acyloxy or acylimidoyl radical containing at least about 34 carbon atoms and (2) at least one radical in which a nitrogen or oxygen atom is attached directly to said radical 1, said nitrogen or oxygen atom also being attached to a hydrocarbon radical or substituted hydrocarbon radical.

5. A composition according to claim 4 wherein the carboxylic acid or anhydride used in step B is maleic anhydride.

6. A composition according to claim 5 wherein the dispersant is a mixed oxygen- and nitrogen-bridged dispersant prepared by sequentially reacting a succinic acid-producing compound having a hydrocarbon-based substituent which contains at least about 50 carbon atoms with at least one alcohol and at least one alkylene polyamine.

7. A composition according to claim 6 wherein the hydrocarbon-based substituent on the succinic acid-producing compound is derived from a polybutenyl or chlorinated polybutenyl polymers.

8. A composition prepared by:
 (A) heating a mixture comprising 2,5-dimercapto-1,3,4-thiadiazole, a mineral oil, and a dispersant which is soluble in said mineral oil and which has a base number less than 7 or an acid number when titrated to a bromphenol blue end point, at a temperature of above about 100° to about 250° C. to yield a homogennous intermediate,
 said dispersant being prepared by sequentially reacting a polybutenyl-substituted succinic acid or anhydride in which the polybutenyl substituent contains at least about 50 carbon atoms and comprises predominantly isobutene units with pentaerythritol and a polyethylene polyamine containing about 3–7 amino groups per molecule,
 about 0.1–10 parts by weight of said dispersant being present per part of 2,5-dimercapto-1,3,4-thiadiazole; and
 (B) reacting the intermediate thus obtained, at a temperature of about 50°–200° C., with maleic anhydride.

9. An additive concentrate comprising a substantially inert, normally liquid organic diluent and from about 20 to 90% by weight of a composition according to claim 1.

10. An additive concentrate comprising a substantially inert, normally liquid organic diluent and from about 20 to 90% by weight of a composition according to claim 2.

11. An additive concentrate comprising a substantially inert, normally liquid organic diluent and from about 20 to 90% by weight of a composition according to claim 4.

12. An additive concentrate comprising a substantially inert, normally liquid organic diluent and from about 20 to 90% by weight of a composition according to claim 5.

13. An additive concentrate comprising a substantially inert, normally liquid organic diluent and from about 20 to 90% by weight of a composition according to claim 7.

14. An additive concentrate comprising a substantially inert, normally liquid organic diluent and from about 20 to 90% by weight of a composition according to claim 8.

15. A lubricating composition comprising a major amount of a lubricating oil and about 0.01 to 20% by weight of said lubricating composition of a composition according to claim 1.

16. A lubricating composition comprising a major amount of a lubricating oil and about 0.01 to 20% by weight of said lubricating composition of a composition according to claim 2.

17. A lubricating composition comprising a major amount of a lubricating oil and about 0.01 to 20% by weight of said lubricating composition of a composition according to claim 4.

18. A lubricating composition comprising a major amount of a lubricating oil and about 0.01 to 20% by weight of said lubricating composition of a composition according to claim 5.

19. A lubricating composition comprising a major amount of a lubricating oil and about 0.01 to 20% by weight of said lubricating composition of a composition according to claim 7.

20. A lubricating composition comprising a major amount of a lubricating oil and about 0.01 to 20% by weight of said lubricating composition of a composition according to claim 8.

* * * * *